United States Patent
Yasui

(10) Patent No.: US 10,844,549 B2
(45) Date of Patent: Nov. 24, 2020

(54) TISSUE PAPER

(71) Applicant: DAIO PAPER CORPORATION, Ehime (JP)

(72) Inventor: Shuta Yasui, Shizuoka (JP)

(73) Assignee: Daio Paper Corporation, Ehime (JP)

( * ) Notice: Subject to any disclaimer, the term of this patent is extended or adjusted under 35 U.S.C. 154(b) by 0 days.

(21) Appl. No.: 16/338,128

(22) PCT Filed: May 23, 2017

(86) PCT No.: PCT/JP2017/019212
§ 371 (c)(1),
(2) Date: Mar. 29, 2019

(87) PCT Pub. No.: WO2018/061309
PCT Pub. Date: Apr. 5, 2018

(65) Prior Publication Data
US 2020/0032459 A1    Jan. 30, 2020

(30) Foreign Application Priority Data
Sep. 30, 2016  (JP) ................. 2016-195200

(51) Int. Cl.
*D21H 27/30* (2006.01)
*A47K 10/16* (2006.01)
*D21H 17/06* (2006.01)
*D21H 17/14* (2006.01)
*D21H 17/24* (2006.01)

(52) U.S. Cl.
CPC ............. *D21H 27/30* (2013.01); *A47K 10/16* (2013.01); *D21H 17/06* (2013.01); *D21H 17/14* (2013.01); *D21H 17/24* (2013.01)

(58) Field of Classification Search
CPC ........ D21H 27/00; D21H 27/30; D21H 17/06; D21H 17/14; D21H 17/22; D21H 17/24; D21H 17/55; D21H 17/07; A47K 2010/3266; A47K 10/16; B32B 29/005; B32B 2307/718; Y10T 428/24934
See application file for complete search history.

(56) References Cited

U.S. PATENT DOCUMENTS

| | | | |
|---|---|---|---|
| 6,623,746 B1 | 9/2003 | Wadle et al. | |
| 8,603,297 B2 * | 12/2013 | Zwick | C11D 3/046 162/158 |
| 10,316,470 B2 * | 6/2019 | Yasui | A47K 7/00 |
| 10,570,568 B2 * | 2/2020 | Yasui | D21H 27/30 |
| 10,618,261 B2 * | 4/2020 | Yasui | D21H 19/12 |
| 2005/0058833 A1 * | 3/2005 | Krzysik | A61K 8/31 428/375 |
| 2005/0100573 A1 * | 5/2005 | Baumoller | D21H 21/22 424/402 |
| 2007/0233024 A1 * | 10/2007 | Uehara | D21H 27/002 604/358 |
| 2008/0207867 A1 | 8/2008 | Uehara et al. | |
| 2008/0223535 A1 * | 9/2008 | Eichhorn | C11D 17/049 162/123 |
| 2009/0314444 A1 * | 12/2009 | Sorns | A61K 8/064 162/135 |
| 2011/0290437 A1 * | 12/2011 | Vogel | D21H 17/20 162/158 |
| 2011/0312236 A1 * | 12/2011 | Bradley | B32B 5/26 442/59 |
| 2012/0297560 A1 * | 11/2012 | Zwick | D04H 1/587 15/104.93 |
| 2013/0101817 A1 * | 4/2013 | Iwasaki | B32B 29/005 428/212 |
| 2013/0337243 A1 * | 12/2013 | Ishikawa | D21H 27/002 428/211.1 |
| 2018/0023255 A1 * | 1/2018 | Yasui | D21H 27/002 424/443 |
| 2018/0030656 A1 * | 2/2018 | Yasui | D21H 27/00 |
| 2018/0258592 A1 * | 9/2018 | Yasui | D21H 27/005 |
| 2018/0272680 A1 * | 9/2018 | Yasui | D21H 21/22 |
| 2020/0010688 A1 * | 1/2020 | Haghdoost | C09D 5/00 |
| 2020/0032459 A1 * | 1/2020 | Yasui | A61Q 19/00 |

FOREIGN PATENT DOCUMENTS

| | | | | |
|---|---|---|---|---|
| EP | 1233107 A1 * | 8/2002 | ............ | B31F 1/07 |
| EP | 3520663 A1 * | 8/2019 | ............ | D21H 17/06 |
| JP | 2002-520511 A | 7/2002 | | |
| JP | 2004188078 A | 7/2004 | | |
| JP | 2008-73118 A | 4/2008 | | |
| JP | 4658056 B2 | 3/2011 | | |
| JP | 4875488 B2 | 2/2012 | | |
| JP | 2013-52142 A | 3/2013 | | |

(Continued)

OTHER PUBLICATIONS

English Translation of International Search Report for PCT/JP2017/019212 dated Jul. 20, 2017, pp. 1-2.

*Primary Examiner* — Jose A Fortuna
(74) *Attorney, Agent, or Firm* — Renner, Kenner; Arthur M. Reginelli

(57) ABSTRACT

In one or more embodiments, the present invention is directed to a moisturizing tissue paper having excellent softness, smoothness, and strength. In various embodiments, the present invention provides a two-ply tissue paper containing a moisturizing agent having a basis weight per ply of 16.6 to 17.9 g/m$^2$, a two-ply paper thickness of 143 to 159 μm, and containing a polyol, hyaluronic acid, a fatty acid ester-based compound, and a fatty acid amide-based compound.

1 Claim, 1 Drawing Sheet

(56) References Cited

FOREIGN PATENT DOCUMENTS

| JP | 2013-192884 A | 9/2013 | |
|---|---|---|---|
| JP | 2016-136978 A | 8/2016 | |
| JP | 6235674 B1 * | 11/2017 | ............ D21H 17/24 |
| WO | 02-066740 A1 | 8/2002 | |
| WO | WO-02066740 A1 * | 8/2002 | ............ D21H 23/22 |
| WO | WO-2012061107 A1 * | 5/2012 | ........... D21H 27/007 |
| WO | WO-2016204078 A1 * | 12/2016 | ............ D21H 21/22 |
| WO | WO-2018061309 A1 * | 4/2018 | ............ D21H 27/00 |

\* cited by examiner

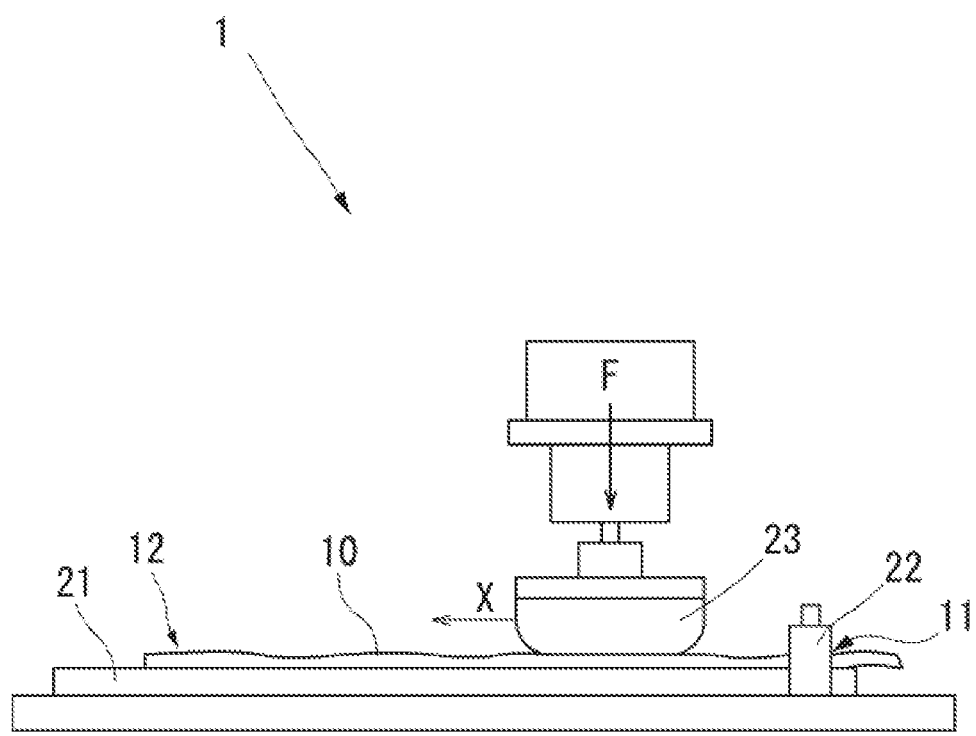

TISSUE PAPER

TECHNICAL FIELD

The present invention relates to a tissue paper, particularly to a tissue paper containing a moisturizing agent.

BACKGROUND ART

Some tissue papers contain a moisturizing agent, and other tissue papers contain no moisturizing agent. A tissue paper containing a moisturizing agent is referred to as a moisturizing tissue, a chemical applied tissue, or the like, is mainly used for direct contact with a skin, for example, for blowing one's nose or removing makeup, and has a moisture content increased by a hygroscopic action of a moisturizing agent.

On the other hand, the quality of a tissue paper is often evaluated by "softness", "smoothness", "thick feeling", and "toughness (strength/secure feeling)". In a moisturizing tissue, "moist feeling" and "sticky feeling" are further adopted as evaluation items in many cases. In other words, in addition to "softness", "smoothness", and "toughness (strength/secure feeling)", a moisturizing tissue also requires excellent "moist feeling" and "sticky feeling".

However, in a moisturizing tissue, as the moisture content is increased due to a moisturizing agent, "softness" which is not felt in a tissue containing no moisturizing agent is felt. However, meanwhile, due to the increase in moisture content, no elasticity is felt, but suppleness is felt, and evaluation of "thick feeling" or "toughness (strength/secure feeling)" is often low. "Softness" and "moist feeling" are enhanced by a moisturizing agent. However, "sticky feeling" due to a chemical is felt at the same time, and evaluation of "sticky feeling" and "smoothness" is often low.

As described above, in evaluation of a moisturizing tissue, for example, an increase in moisture content, which mainly increases evaluation of "softness" or "moist feeling", often lowers evaluation of "sticky feeling", "smoothness", and "toughness (strength/secure feeling)". It is difficult to improve both of these. Particularly, it is difficult to improve "moist feeling" and "smoothness" so as to be felt remarkably and to improve "toughness (strength/secure feeling)" at the same time.

On the other hand, quality of a tissue paper is evaluated by a sensory test. However, a person easily confuses evaluation items particularly in a moisturizing tissue as a feeling. For example, a tissue evaluated to have "softness" by one subject may be evaluated to have "moist feeling" by another subject. For this reason, in a moisturizing tissue, a latent sensory difference is easily generated in evaluation by a subject. For this reason, it is difficult to develop a tissue paper improving both of the above evaluation items.

CITATION LIST

Patent Literature

JP 4875488 B2, JP 4450552 B2, JP 4658056 B2 are indicated as prior art related to the present invention.

SUMMARY OF INVENTION

Technical Problem

Therefore, a main object of the present invention is to provide a moisturizing tissue having excellent quality concerning sensory performance, particularly having excellent quality concerning sensory performance in actual use by a user, particularly having excellent "texture" such as "moist feeling" or "smoothness" and having "toughness (strength/secure feeling)".

Solution to Problem

Means for solving the above problems are as follows.
[Invention According to Claim 1]
A two-ply tissue paper comprising a moisturizing agent, wherein
a basis weight per ply is 16.6 to 17.9 g/m$^2$,
a two-ply paper thickness is 143 to 159 μm,
all of a polyol, hyaluronic acid, a fatty acid ester-based compound, and a fatty acid amide-based compound are contained,
the content of a fatty acid ester-based compound is 0.10 to 0.50 parts by mass with respect to 100 parts by mass of a pulp fiber and the content of a fatty acid amide-based compound is 0.01 to 0.05 parts by mass with respect to 100 parts by mass of a pulp fiber,
a wet tensile strength in CD is 36 cN/25 mm or more, and
an evaluation value (T) determined by the following formula (1) is 97 or more, Evaluation value (T)=(basis weight×two-ply paper thickness×moisture content)/(dry tensile strength in MD (machine direction)×dynamic friction coefficient average value measured by a pin-on-plate type friction test apparatus×friction coefficient maximum value measured by a pin-on-plate type friction test apparatus)   (1).

Advantageous Effects of Invention

The present invention described above provides a moisturizing tissue having excellent quality concerning sensory performance, particularly having excellent quality concerning sensory performance in actual use by a user, particularly having excellent "texture" such as "moist feeling" or "smoothness" and having "toughness (strength/secure feeling)".

BRIEF DESCRIPTION OF DRAWINGS

FIG. 1 is a view for explaining a method for measuring of a dynamic friction coefficient average value according to the present invention.

DESCRIPTION OF EMBODIMENTS

Hereinafter, an embodiment of the present invention will be described.

A tissue paper according to the present invention is a tissue paper containing a moisturizing agent, also referred to as a moisturizing tissue, a lotion tissue, a chemical applied tissue, or the like. The moisturizing agent according to the present invention mainly contains a polyol having a function of taking moisture into a paper due to a hygroscopic property thereof to increase a moisture content. Therefore, the tissue paper according to the present invention contains a polyol. Examples of the polyol according to the present invention include glycerin, diglycerin, propylene glycol, 1,3-butylene glycol, polyethylene glycol, sorbitol, glucose, xylitol, maltose, maltitol, mannitol, and trehalose. Among these polyols, glycerin and diglycerin are preferable.

The tissue paper according to the present invention contains a hyaluronic acid. The hyaluronic acid is also a component of the moisturizing agent. By containing hyaluronic acid, moist feeling and thick feeling are enhanced as compared with a case where only a polyol is contained. A reason for this is not clear, but is estimated to be that hyaluronic acid makes evaporation of moisture absorbed by a polyol difficult and further tends to have a high viscosity.

The content of a polyol in the moisturizing agent according to the present invention is more than 80.0% by mass to less than 85.0% by mass, and preferably more than 81.5% by mass to less than 85.0% by mass. The content of hyaluronic acid is 0.010% by mass or more to 0.030% by mass or less, and preferably 0.020% by mass or more to 0.030% by mass or less. Within these ranges of the contents of a polyol and hyaluronic acid, the effect of the present invention is exhibited.

In order to make the tissue paper according to the present invention contain a polyol and hyaluronic acid, a polyol and hyaluronic acid are preferably added externally to a base paper as a moisturizing chemical. A chemical can be externally added to a base paper by a known technique such as spray application, printing application, or roll transfer. A polyol and hyaluronic acid can be mixed and added or separately added to a base paper.

On the other hand, the tissue paper according to the present invention contains a fatty acid ester-based compound and a fatty acid amide-based compound together with the above polyol and hyaluronic acid. The fatty acid ester-based compound has an effect of improving wettability and plumpness (fluffiness) of a surface of the tissue paper, and the fatty acid amide-based compound has an effect of coating a fiber surface. The tissue paper according to the present invention has excellent softness of a base paper itself and excellent surface smoothness by using these compounds.

Here, the fatty acid ester-based compound may be either a cationic fatty acid ester-based compound or a nonionic fatty acid ester-based compound, but it is desirable that both of these compounds are contained. It is desirable that the fatty acid ester-based compound is a compound of an alcohol having 6 to 24 carbon atoms and a fatty acid having 7 to 25 carbon atoms. The alcohol may be any one of a linear alcohol, a branched alcohol, a saturated alcohol, and an unsaturated alcohol. Particularly, an alcohol having 10 to 22 carbon atoms is preferable, and lauryl alcohol, myristyl alcohol, cetyl alcohol, stearyl alcohol, behenyl alcohol, and oleyl alcohol are preferable. These alcohols may be used singly or in combination of two or more kinds thereof. The fatty acid having 7 to 25 carbon atoms may be any one of a linear fatty acid, a branched fatty acid, a saturated fatty acid, and an unsaturated fatty acid. Particularly, a fatty acid having 10 to 22 carbon atoms is preferable, and lauric acid, myristic acid, palmitic acid, stearic acid, behenic acid, and oleic acid are preferable. These fatty acids may be used singly or in combination of two or more kinds thereof.

The fatty acid amide-based compound can be obtained by a reaction between a polyalkylene polyamine and a carboxylic acid. A suitable polyalkylene polyamine is a compound having at least three amino groups in a molecule thereof, represented by the following formula (1).

$$H_2N-(R_1-NH-)_n-R_1-NH_2 \qquad (1)$$

($R_1$s each independently represent an alkylene group having 1 to 4 carbon atoms, and n represents an integer of 1 to 3)

In this polyacrylic amine, different $R_1$s may exist in a molecule thereof. Two or more polyalkylene polyamines can also be used. $R_1$ is preferably an ethylene group. It is desirable that the carboxylic acid is a carboxylic acid having 10 to 24 carbon atoms. The carboxylic acid may be either a saturated carboxylic acid or an unsaturated carboxylic acid. The carboxylic acid may be either a linear carboxylic acid or a branched carboxylic acid. Among these carboxylic acids, a carboxylic acid having 12 to 22 carbon atoms is preferable, and a carboxylic acid having 14 to 18 carbon atoms is particularly preferable.

In the tissue paper according to the present invention, it is desirable that the content of a fatty acid ester-based compound is 0.10 to 0.50 parts by mass with respect to 100 parts by mass of a pulp fiber and the content of a fatty acid amide-based compound is 0.01 to 0.05 parts by mass with respect to 100 parts by mass of a pulp fiber.

In order to make the tissue paper according to the present invention contain a fatty acid ester compound and a fatty acid amide compound, it is preferable to add these compounds internally in the form of a mixture of these compounds or separately as a softener compound at the time of making a base paper. This makes a fatty acid ester-based compound adapt to a pulp fiber and promotes an effect of coating the pulp fiber by a fatty acid amide-based compound when a wet paper is dried with a yankee drier. As a result, a tissue paper having excellent smoothness is obtained. A position to add a softener compound internally to a paper-making raw material or a wet paper at the time of paper making can be an appropriate position. For example, a softener compound can be added at the position of a mixing tank, a machine tank, or a seed box.

The tissue paper according to the present invention has excellent flexibility and smoothness of a base paper itself due to a fatty acid ester-based compound and a fatty acid amide-based compound. Therefore, the tissue paper according to the present invention has extremely good softness and smoothness because of an increase in moisture content due to a hygroscopic property of a polyol and exhibition of softness due to an effect of hyaluronic acid. In addition, since the base paper itself has excellent flexibility and smoothness, the tissue paper according to the present invention is a moisturizing tissue paper having an increased moisture content due to a hygroscopic property, but can have excellent toughness. Particularly, the tissue paper according to the present invention has excellent softness and smoothness in a moisturizing tissue paper, and also has toughness because of containing hyaluronic acid.

Here, it is desirable that the tissue paper according to the present invention further contains polyamide epichlorohydrin and at least one of polyacrylamide and cationic starch together with a fatty acid ester-based compound and a fatty acid amide-based compound. Polyamide epichlorohydrin acts as a wet paper strength agent, and polyacrylamide and cationic starch act as a dry paper strength agent. The polyamide epichlorohydrin, polyacrylamide, and cationic starch can effectively improve paper strength without inhibiting an effect of improving softness and smoothness by a polyol, hyaluronic acid, a fatty acid ester-based compound, and a fatty acid amide-based compound. By using the polyamide epichlorohydrin, polyacrylamide, and cationic starch, the tissue paper according to the present invention has better softness and smoothness, has improved strength, and has a very high sensory evaluation value by a consumer.

It is desirable that the content of polyamide epichlorohydrin is 0.1 to 1.0 part by mass with respect to 100 parts by mass of a pulp fiber and the content of at least one of polyacrylamide and cationic starch is 0.01 to 0.20 parts by mass with respect to 100 parts by mass of a pulp fiber.

In order to make the tissue paper according to the present invention contain polyamide epichlorohydrin and at least one of polyacrylamide and cationic starch, it is preferable to add these compounds internally by mixing these compounds or separately at the time of making base paper like a fatty acid ester compound and a fatty acid amide compound. A position to add these compounds internally to a papermaking raw material or a wet paper at the time of paper making can be an appropriate position.

On the other hand, in a case where the tissue paper according to the present invention contains polyamide epichlorohydrin and at least one of polyacrylamide and cationic starch, particularly, it is desirable that a ratio ((B)/(A)) of the total content (B) of a fatty acid ester-based compound and a fatty acid amide-based compound to the total content (A) of polyamide epichlorohydrin and at least one of polyacrylamide and cationic starch is 0.75 or more. In a case where the tissue paper according to the present invention contains these compounds at this ratio, particularly, the tissue paper has excellent softness, smoothness, and strength. It is considered that a balance between an effect of exhibiting softness and smoothness of the base paper itself by a fatty acid ester-based compound and a fatty acid amide-based compound and improvement of paper strength is good to make a sensory evaluation value by a consumer very high.

Furthermore, in a case where the tissue paper according to the present invention contains polyamide epichlorohydrin and at least one of polyacrylamide and cationic starch, it is desirable that a ratio of the content of the fatty acid ester-based compound to the total content of the fatty acid amide-based compound, polyamide epichlorohydrin, and polyacrylamide ((fatty acid ester-based compound)/(fatty acid amide-based compound+polyamide epichlorohydrin+at least one of polyacrylamide and cationic starch)) is 0.40 or more. Also in this case, a balance between effects of improving softness, smoothness and strength is excellent to make a sensory evaluation value by a consumer very high.

The number of plies of the tissue paper according to the present invention is two, and the basis weight per ply is 16.6 to 17.9 g/m$^2$. The two-ply paper thickness is 143 to 159 μm. The tissue paper according to the present invention has sufficient strength in a case of two plies. In the above ranges of the basis weight and the paper thickness, effects of a polyol, hyaluronic acid, a fatty acid ester compound, and a fatty acid amide compound are remarkable, and a tissue paper having excellent softness, smoothness, and toughness is obtained. Here, the basis weight in the present invention means a value measured according to JIS P 8124 (1998). The paper thickness means a value obtained by sufficiently subjecting a test piece to humidity control under conditions of JIS P 8111 (1998), and then measuring the paper thickness using a dial thickness gauge (thickness measuring instrument) "PEACOCK G type" (manufactured by Ozaki MFG. Co., Ltd.) under the same conditions. Specifically, the paper thickness is measured by confirming that there is no rubbish, dust, or the like between a plunger and a measuring table, placing the plunger on the measuring table, moving a scale of the dial thickness gauge to adjust a zero point, then raising the plunger, placing a sample on a test table, lowering the plunger slowly, and reading the current gauge. At this time, the plunger is only placed thereon. A terminal of the plunger is made of metal, and a circular plane thereof with a diameter of 10 mm contacts perpendicularly to a paper plane, and a load at the time of measuring the paper thickness is about 70 gf. The paper thickness is an average value in 10 times of measurements.

On the other hand, the tissue paper according to the present invention has an evaluation value (T) determined by the following formula (1) of 97 or more.

Evaluation value (T)=(basis weight×two-ply paper thickness×moisture content)/(dry tensile strength in MD (machine direction)×dynamic friction coefficient average value measured by a pin-on-plate type friction test apparatus×friction coefficient maximum value measured by a pin-on-plate type friction test apparatus) (1).

The two-ply tissue paper according to the present invention, having a basis weight per ply of 16.6 to 17.9 g/m$^2$, having a two-ply paper thickness of 143 to 159 μm, and containing all of a polyol, hyaluronic acid, a fatty acid ester-based compound, and a fatty acid amide-based compound can have an evaluation value (T) of 97 or more in the above evaluation formula (the above formula (1)) (hereinafter also simply referred to as "evaluation formula"). A tissue paper satisfying this evaluation value (T) is extremely good in quality evaluation. A relationship between the evaluation value (T) and the quality evaluation of a tissue paper will be described. The quality evaluation of a tissue paper, particularly a moisturizing tissue paper is generally performed by sensory evaluation imitating a scene of use by an actual user. However, for example, three evaluations of "softness", "smoothness", and "moist feeling", two evaluations of "moist feeling" and "sticky feeling", and two evaluations of "thick feeling" and "toughness (strength/secure feeling)" are sensuously close to each other. Therefore, there are variations in criteria depending on a subject to perform sensory evaluation.

Therefore, the present inventors performed a unique sensory evaluation test for deriving the above evaluation formula according to the present invention for a large number of tissue papers currently available, including commercially available products, and also measured various physical property values which will affect quality evaluation of a tissue paper, for example, known physical property values such as a basis weight, a paper thickness, a moisture content, softness, and dry tensile strength, and friction characteristics including the dynamic friction coefficient average value and the friction coefficient maximum value according to the present invention. In the sensory evaluation test according to the present invention, various tissue papers as samples were handed in random order to each subject, and each subject used the tissue papers by a free method decided by the subject him/herself, for example, the subject blew his/her nose, touched the tissue papers with hands, or wiped something with the tissue papers. Under a free usage mode of the subject, the subject ranked each tissue paper as a sample with only criteria of "favorable" and "unfavorable". A value obtained by dividing the sum of the ranked points for each sample by the number of subjects was used as a sensory evaluation value. In this sensory evaluation test, an impression of use of a tissue paper in a free usage mode is evaluated, and the quality concerning sensory performance at the time of use is remarkably reflected, whereas a sensory test so far was performed for each of "softness", "smoothness", "thick feeling", "toughness (strength/secure feeling)", "moist feeling", and "sticky feeling", and each of these items or the sum thereof was used as an evaluation value. A correlation among the sensory evaluation value according to the present invention, the above various material values, and the measured values relating to friction was analyzed by regression analysis. It was confirmed that "unit weight", "two-ply paper thickness", "moisture content", "dry tensile strength in MD", "friction coefficient average value", and "friction coefficient maximum value" were independent of each other and had a high correlation with the sensory evaluation value. Then, the above evaluation formula was created using the "positive/negative correlation" between the sensory evaluation value and each measured physical property value and the strength. Regarding an evaluation value calculated by this formula and the sensory evaluation value, a constant regression formula having a high determination coefficient is obtained. A tissue paper having a high sensory evaluation value not found in a conventional product based on this regression formula has been found in the two-ply tissue paper according to the present invention, having a basis weight per ply of 16.6 to 17.9 g/m$^2$, having a two-ply paper thickness of 140 to 175 μm, and containing all of a polyol, hyaluronic acid, a fatty acid ester-based compound, and a fatty acid amide-based compound.

A moisturizing tissue paper which acquired high evaluation in an evaluation value (T) in this evaluation formula was further studied, and was found particularly in a case where a tissue paper contained polyamide epichlorohydrin and at least one of polyacrylamide and cationic starch together with the fatty acid ester-based compound and the fatty acid amide-based compound, in a case where a ratio ((B)/(A)) of the total content (B) of the fatty acid ester-based compound and the fatty acid amide-based compound to the total content (A) of polyamide epichlorohydrin and at least one of polyacrylamide and cationic starch was 0.75 or more, and in a case where a ratio of the content of the fatty acid ester-based compound to the total content of the fatty acid amide-based compound, polyamide epichlorohydrin, and polyacrylamide ((fatty acid ester-based compound)/(fatty acid amide-based compound+polyamide epichlorohydrin+at least one of polyacrylamide and cationic starch)) was 0.40 or more.

Here, the dry tensile strength among the physical property values examining the correlation with the sensory evaluation test according to the present invention was measured with a sample width of 25 mm based on a tensile test of JIS P 8113 (1998). Softness was measured based on a handle-o-meter method according to a JIS L 1096 (2010) E method.

The dynamic friction coefficient average value and the friction coefficient maximum value according to the present invention can be measured using a pin-on-plate type friction test apparatus 1 illustrated in FIG. 1. The pin-on-plate type friction test apparatus may be any one as long as a sliding speed can be appropriately selected from values of 0.1 to 100.0 mm/s, a vertical load can be appropriately selected from values of 0 to 1 kgf, and a sliding distance can be appropriately selected from values of 1 to 200 mm.

In the measurement of the dynamic friction coefficient average value and the friction coefficient maximum value according to the present invention, as illustrated in the drawing, first, a tissue paper 10 as a sample having a sufficient size is placed on a horizontal plate 21 of the pin-on-plate type friction test apparatus 1, and one side edge portion 11 thereof is fixed with a jig 22 or the like. Thereafter, on the tissue paper 10, a contactor 23 is horizontally moved while being in contact with the tissue paper 10 from a fixed direction toward a direction of a non-fixed edge portion 12 (X direction in the drawing) at a sliding speed of 1.0 mm/s, a vertical load F of 50 gf, and a sliding distance of 5.0 mm, and a dynamic friction coefficient average value and a dynamic friction coefficient maximum value at this time are measured. The dynamic friction coefficient average value and the friction coefficient maximum value are an average value and a maximum value of a friction coefficient of each tissue paper sample at a sliding distance of 4 to 5 mm, respectively.

Measurement conditions are experimental room temperature of 20° C. and laboratory humidity of 20 RH %. A lubrication condition is a non-lubricated condition in the atmosphere. A measurement sample is allowed to stand for 24 hours in a chamber at 25° C. and 20% RH to be subjected to a test. At the time of measurement, the movement of the contactor 23 is performed not by sliding the contactor 23 reciprocally but by sliding the contactor 23 in one way. The contactor 23 is made of a soft urethane material having a contact area equal to or larger than the fingertip of a person and having a hardness almost equal to the finger of a person, and obtained by forming a plurality of grooves almost equal to a human fingerprint in the urethane material in a direction orthogonal to a moving direction. Specific examples of an apparatus for performing this measurement include Tribomaster TYPE μv 1000 manufactured by Trinity-Lab. Inc. With this apparatus, it is only required to perform measurement using an optional "sensory contactor" manufactured by Trinity-Lab. Inc. for the contactor.

On the other hand, in tissue paper according to the present invention, it is preferable to adjust a crepe ratio at the time of manufacture in a range of 13 to 20%. It is desirable that the pulp fiber is obtained by blending needle bleached kraft pulp (NBKP) and leaf bleached kraft pulp (LBKP). Particularly, the pulp fiber preferably contains only NBKP and LBKP. A blend ratio thereof is preferably NBKP:LBKP=20:80 to 80:20, and particularly desirably NBKP:LBKP=30:70 to 60:40.

Note that the tissue paper according to the present invention is suitable for use as a pop-up type tissue paper product contained in a storage box also called a carton box. In this case, in order to form a bundle of pop-up type tissue papers to be contained in the storage box, it is desirable to use a rotary type inter folder having excellent folding quality.

EXAMPLES

Subsequently, for Examples 1 to 6 of the tissue paper according to the present invention, Reference Example 1 and Comparative Examples 1 to 7, physical property values of a basis weight, a paper thickness, dry and wet tensile strengths in MD and CD (cross direction), elongation, softness, MMD, a dynamic friction coefficient maximum value, a dynamic friction coefficient minimum value, and a dynamic friction coefficient average value were measured, and the sensory evaluation test according to the present invention was performed. Comparative Examples 1 to 3 are commercially available non-moisturizing tissues, and Comparative Examples 4 to 7 are moisturizing tissues including commercial products. As the polyol, glycerin was used. As the softener compound containing a fatty acid ester-based compound, a compound of an alcohol having 6 to 24 carbon atoms and a fatty acid having 7 to 25 carbon atoms was used. As the softener compound containing a fatty acid amide-based compound, a softener compound containing a fatty acid amide-based compound obtainable by a reaction between a polyalkylene polyamine and a carboxylic acid was used. Composition/physical property values in each Example are as illustrated in Table 1 below.

In a method for measuring MMD, while a contact surface of a friction element is brought into contact with a surface of a measurement sample to which a tension of 20 g/cm is applied in a predetermined direction at a contact pressure of 25 g, the measurement sample is moved by 2 cm in substantially the same direction as the direction in which the tension is applied at a speed of 0.1 cm/s, and a friction coefficient at this time is measured using a friction sense tester KES-SE (manufactured by Kato Tech Co., Ltd.). A value obtained by dividing the friction coefficient by a friction distance (moving distance=2 cm) is MMD. The friction element is formed by adjoining 20 piano wires P each having a diameter of 0.5 mm, and has a contact surface formed such that the length and the width were both 10 mm. On the contact surface, a unit bulging portion having a tip formed with 20 piano wires P (radius of curvature: 0.25 mm) is formed.

Elongation is based on JIS P 8113 (1998).

For sensory evaluation values, 31 subjects were subjected to a test. As a method for the test, two-ply tissue papers as samples in Examples were handed in random order to each subject, and each subject used the tissue papers by a free method decided by the subject him/herself, for example, the subject blew his/her nose, touched the tissue papers with hands, or wiped something with the tissue papers. The subject ranked each tissue paper with only criteria of "favorable" and "unfavorable". One piece of paper in Comparative Example 6 with the sample name hidden was ranked as four points of a reference sample, and the papers were ranked with natural numbers of one to seven points. The sum of the points was used as a sensory evaluation value.

TABLE 1

| | | | Reference Ex. 1 | Ex. 1 | Ex. 2 | Ex. 3 | Ex. 4 | Ex. 5 | Ex. 6 |
|---|---|---|---|---|---|---|---|---|---|
| Blending of pulp | NBKP | % by mass | 40 | 40 | 40 | 50 | 50 | 40 | 40 |
| | LBKP | % by mass | 60 | 60 | 60 | 50 | 50 | 60 | 60 |
| Crepe ratio | | % | 15.0 | 15.0 | 13.5 | 13.5 | 16.0 | 13.0 | 13.0 |
| Softener compound containing fatty acid ester-based compound | | Parts by mass | 0.10 | 0.10 | 0.20 | 0.35 | 0.50 | 0.45 | 0.45 |
| Softener compound containing fatty acid amide-based compound | | Parts by mass | 0.05 | 0.05 | 0.05 | 0.01 | 0.02 | 0.04 | 0.04 |
| Wet paper strength agent | Polyamide epichlorohydrin | Parts by mass | 0.15 | 0.15 | 0.15 | 0.10 | 0.14 | 0.15 | 0.15 |
| Dry paper strength agent | Polyacrylamide | Parts by mass | 0.05 | 0.05 | 0.03 | — | 0.05 | 0.02 | 0.02 |
| Dry paper strength agent | Cationic starch | Parts by mass | — | — | — | 0.03 | — | — | — |
| Polyol | | % by mass | 80.8 | 83.6 | 81.4 | 82.0 | 83.2 | 82.7 | 84.8 |
| Hyaluronic acid | | % by mass | 0.010 | 0.020 | 0.010 | 0.025 | 0.010 | 0.015 | 0.030 |
| Water | | % by mass | 15.0 | 15.0 | 15.0 | 15.0 | 15.0 | 15.0 | 15.0 |
| Others | | % by mass | 4.19 | 1.38 | 3.59 | 2.97 | 1.79 | 2.29 | 0.17 |
| Basis weight (1P) | | g/m$^2$ | 15.9 | 16.6 | 17.4 | 16.9 | 17.1 | 16.9 | 17.9 |
| Paper thickness (2P) | | μm | 151 | 159 | 152 | 149 | 159 | 143 | 158 |
| Density (2P) | | g/cm$^3$ | 0.21 | 0.21 | 0.23 | 0.23 | 0.22 | 0.24 | 0.23 |
| Dry tensile strength(MD)2P | | cN/25 mm | 214 | 218 | 229 | 180 | 199 | 170 | 131 |
| Dry tensile strength(CD)2P: A | | cN/25 mm | 85 | 70 | 72 | 68 | 73 | 60 | 52 |
| Wet tensile strength(CD)2P: B | | cN/25 mm | 47 | 36 | 41 | 45 | 42 | 44 | 38 |
| B/A | | cN/25 mm | 0.55 | 0.51 | 0.57 | 0.66 | 0.58 | 0.73 | 0.73 |
| Softness | | cN/100 mm | 0.80 | 0.75 | 0.86 | 0.90 | 0.88 | 0.93 | 0.93 |
| MMD (contact surface) | | 1/100 | 7.3 | 6.9 | 6.4 | 6.0 | 5.5 | 6.9 | 6.2 |
| Water content | | % by mass | 12.1 | 12.8 | 11.8 | 10.8 | 12.6 | 13.1 | 13.6 |
| Dynamic friction coefficient average value | | — | 1.02 | 0.87 | 1.03 | 1.13 | 0.95 | 1.18 | 1.16 |
| Friction coefficient maximum value | | — | 1.26 | 1.10 | 1.27 | 1.38 | 1.20 | 1.42 | 1.36 |
| Friction coefficient minimum value | | — | 0.79 | 0.51 | 0.67 | 0.74 | 0.57 | 0.64 | 0.81 |
| Touch coefficient | | — | 106 | 162 | 104 | 97 | 151 | 111 | 186 |
| Sensory evaluation value | | — | 117 | 173 | 129 | 162 | 166 | 138 | 185 |

| | | | Compar. Example 1 | Compar. Example 2 | Compar. Example 3 | Compar. Example 4 | Compar. Example 5 | Compar. Example 6 | Compar. Example 7 |
|---|---|---|---|---|---|---|---|---|---|
| Blending of pulp | NBKP | % by mass | 30 | 30 | 30 | 30 | 30 | 50 | 40 |
| | LBKP | % by mass | 70 | 70 | 70 | 70 | 70 | 50 | 60 |
| Crepe ratio | | % | 16.0 | 18.0 | 15.0 | 13.5 | 15.0 | 15.0 | 14.5 |
| Softener compound containing fatty acid ester-based compound | | Parts by mass | — | 0.10 | — | — | — | 0.08 | 0.05 |
| Softener compound containing fatty acid amide-based compound | | Parts by mass | — | 0.02 | — | — | — | 0.05 | 0.01 |
| Wet paper strength agent | Polyamide epichlorohydrin | Parts by mass | 0.10 | 0.15 | 0.10 | 0.10 | 0.05 | 0.10 | 0.15 |
| Dry paper strength agent | Polyacrylamide | Parts by mass | 0.05 | 0.03 | 0.02 | 0.05 | 0.05 | 0.05 | 0.05 |
| Dry paper strength agent | Cationic starch | Parts by mass | — | — | 0.03 | — | — | — | — |
| Polyol | | % by mass | — | — | — | 85.0 | 80.0 | 80.0 | 80.0 |
| Hyaluronic acid | | % by mass | — | — | — | — | — | — | — |
| Water | | % by mass | — | — | — | 10.0 | 15.0 | 10.0 | 10.0 |
| Others | | % by mass | — | — | — | 5.00 | 5.00 | 10.00 | 10.00 |
| Basis weight (1P) | | g/m$^2$ | 10.5 | 12 | 16.1 | 14.6 | 14.53 | 18.1 | 16.5 |
| Paper thickness (2P) | | μm | 116 | 123 | 200 | 139 | 141 | 172 | 167 |
| Density (2P) | | g/cm$^3$ | 0.18 | 0.20 | 0.16 | 0.21 | 0.21 | 0.21 | 0.20 |
| Dry tensile strength(MD)2P | | cN/25 mm | 376 | 235 | 289 | 221 | 279 | 216 | 183 |
| Dry tensile strength(CD)2P: A | | cN/25 mm | 123 | 80 | 98 | 83 | 86 | 60 | 57 |
| Wet tensile strength(CD)2P: B | | cN/25 mm | 35 | 30 | 37 | 51 | 38 | 32 | 33 |
| B/A | | cN/25 mm | 0.28 | 0.38 | 0.38 | 0.61 | 0.44 | 0.53 | 0.58 |
| Softness | | cN/100 mm | 0.90 | 0.94 | 1.10 | 0.81 | 0.80 | 1.00 | 0.80 |

TABLE 1-continued

| | | | | | | | | |
|---|---|---|---|---|---|---|---|---|
| MMD (contact surface) | 1/100 | 8 | 6.5 | 5.7 | 8.3 | 7.3 | 4.8 | 5.1 |
| Water content | % by mass | 4.5 | 4.1 | 6.1 | 11.3 | 11.7 | 11.2 | 10.6 |
| Dynamic friction coefficient average value | — | 1.71 | 1.44 | 1.53 | 1.29 | 1.02 | 1.28 | 1.33 |
| Friction coefficient maximum value | — | 1.97 | 1.71 | 1.79 | 1.56 | 1.21 | 1.54 | 1.62 |
| Friction coefficient minimum value | — | 1.23 | 0.95 | 1.06 | 0.86 | 0.65 | 0.86 | 0.88 |
| Touch coefficient | — | 4 | 10 | 25 | 52 | 70 | 82 | 74 |
| Sensory evaluation value | — | 53 | 60 | 62 | 81 | 108 | 124 | 120 |

The results in Table 1 indicate that Examples 1 to 6 have high sensory evaluation values among the Examples. Meanwhile, Comparative Examples 6 and 7 have lower wet tensile strength in CD and a higher dynamic friction coefficient average value than those in Examples according to the present invention. In addition, the sensory evaluation value and the evaluation value (T) according to the present invention are also low. Therefore, Comparative Examples 6 and 7 are inferior in smoothness and toughness and also inferior in sensory performance quality to Examples. Comparative Examples 1 to 5 have significantly low evaluation values (T) and have low sensory evaluation values similarly. Particularly in each of Comparative Examples 1 to 7, the evaluation value (T) according to the present invention is not 95 or more.

From the above, the tissue paper according to the present invention is a moisturizing tissue having excellent "texture" such as "moist feeling" or "smoothness" and having "toughness (strength/secure feeling)", and is a moisturizing tissue having extremely good quality concerning sensory performance, particularly having extremely good quality concerning sensory performance in actual use by a user.

REFERENCE SIGNS LIST

1 Apparatus for measuring dynamic friction coefficient average value
10 Tissue paper sample
21 Plate
22 Jig
23 Contactor

The invention claimed is:

1. A two-ply tissue paper comprising a moisturizing agent, wherein
a basis weight per ply is 16.6 to 17.9 g/m$^2$,
a two-ply paper thickness is 143 to 159 μm, and
all of a polyol, hyaluronic acid, a fatty acid ester-based compound, and a fatty acid amide-based compound are contained in the two-ply tissue paper,
the content of a fatty acid ester-based compound is 0.10 to 0.50 parts by mass with respect to 100 parts by mass of a pulp fiber and the content of a fatty acid amide-based compound is 0.01 to 0.05 parts by mass with respect to 100 parts by mass of a pulp fiber,
a wet tensile strength in CD is 36 cN/25 mm or more, and
an evaluation value (T) determined by the following formula (1) is 97 or more, Evaluation value (*T*)=(basis weight×two-ply paper thickness×moisture content)/(dry tensile strength in MD (machine direction)×dynamic friction coefficient average value measured by a pin-on-plate type friction test apparatus×friction coefficient maximum value measured by a pin-on-plate type friction test apparatus)  (1).

* * * * *